United States Patent [19]

Galib

[11] Patent Number: 4,995,880
[45] Date of Patent: Feb. 26, 1991

[54] INTRAOCULAR LENS AND METHOD OF SURGICALLY IMPLANTING SAME IN AN EYE

[76] Inventor: Samuel H. Galib, 104 Morlyn Rd., Bryn Mawr, Pa. 19010

[21] Appl. No.: 412,487

[22] Filed: Sep. 26, 1989

[51] Int. Cl.$^5$ .............................................. A61F 2/16
[52] U.S. Cl. ....................................................... 623/6
[58] Field of Search ............................................ 623/6

[56] References Cited

U.S. PATENT DOCUMENTS

| | | | |
|---|---|---|---|
| 4,373,218 | 2/1983 | Schachar | 623/6 |
| 4,585,457 | 4/1986 | Kalb | 623/6 |
| 4,693,717 | 9/1987 | Michelson | 623/6 |
| 4,822,360 | 4/1989 | Deacon | 623/6 |

FOREIGN PATENT DOCUMENTS

| 0328117 | 8/1989 | European Pat. Off. | 623/6 |
|---|---|---|---|

*Primary Examiner*—Ronald Frinks
*Attorney, Agent, or Firm*—William Freedman; Morton C. Jacobs

[57] ABSTRACT

In this method an artificial lens is implanted in an eye in which the crystalline portion of the natural lens has been surgically removed through an opening made in the anterior wall of the lens capsule and through a small incision in ocular tissue at the front of the eye. This method utilizes an expansible bag that has a transparent body portion containing a cavity and an entrance opening to the cavity through which filler material can be introduced into the body portion. The body portion of the bag is inserted through the small incision and through said opening in the anterior wall of the lens capsule into a position where at least a portion of the body portion is located within the still-remaining portion of the lens capsule. Then the body portion is distended by introducing filler material through said entrance opening, and the distended body portion is located within the still-remaining portion of the lens capsule in a location adjacent the posterior wall of the capsule.

27 Claims, 4 Drawing Sheets

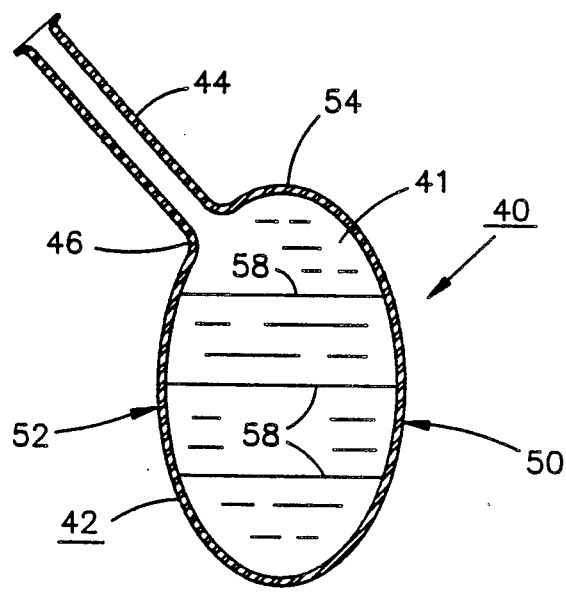
Fig. 3
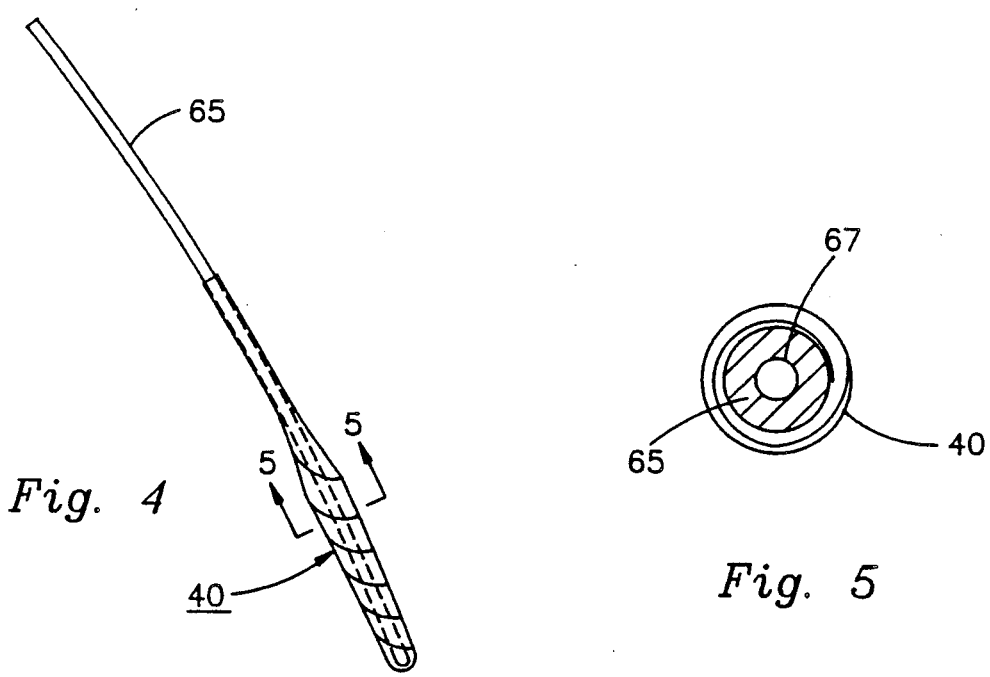
Fig. 4
Fig. 5

INTRAOCULAR LENS AND METHOD OF SURGICALLY IMPLANTING SAME IN AN EYE

BACKGROUND

This invention relates to an intraocular lens and, more particularly, to an intraocular lens that can be surgically implanted in an eye through a very small incision. The invention also relates to a method of surgically implanting such a lens.

In the human eye, the natural lens is situated behind the pupil and iris, and it serves to focus light entering through the cornea and pupil onto the retina at the rear of the eye. The natural lens comprises a biconvex crystalline structure, normally highly transparent, and a lens capsule surrounding the crystalline structure. The lens is supported at its outer periphery by suspensory ligaments, called zonules, that are connected between the lens capsule and the surrounding ciliary muscle.

A cataract condition is present when the material within the lens capsule becomes cloudy, as a result, for example, of age, trauma, or some metabolic problem. As the lens clouds, light passing through it is reduced, and vision becomes progressively blurrier as this clouding increases.

Technology and methods exist today that enable a surgeon to remove the clouded natural lens, or cataract, through a relatively small incision 3 or 4 millimeters (mm) or less made near the periphery of the cornea. In small-incision extra-capsular cataract extraction, the surgeon enters the eye through this small incision, makes an opening through the front wall, or anterior capsule, of the lens, and then removes the clouded cellular material through this opening and the small incision. Various techniques are available for effecting such removal, one of which is called phaco-emulsification. This involves ultrasonic fragmentation of the nucleus of the cataract into small particles and removal of such particles by suction, all of which is effected through a slender, hollow phaco-emulsification tip inserted through the small incision. The remainder of the cataractous material is removed through use of a slender irrigation and aspiration tip also inserted through the small incision; and when this removal step is completed, there is left a clean lens capsule free from cataractous material.

The next step in this surgical procedure is to introduce an artificial lens into the space formerly occupied by the crystalline portion of the natural lens. The vast majority of intraocular lens implants used today have a lens body composed of a rigid material with a diameter of 6 mm or more. Insertion of such an implant requires enlargement of the 3 or 4 mm small incision to allow for entry of the implant, thus defeating many of the advantages of the small incision. Among these advantages are more rapid healing, less astigmatic induction, less deformation of the shape of the globe, and more rapid restoration of the patient to active life with less post-operative discomfort.

Numerous proposals have been made to provide intraocular implants that can be inserted and positioned through the above-described small incision. For example, there are available foldable implants that are inserted in a folded condition through the incision and then unfolded while in the eye. These foldable implants are cumbersome to insert and position, oftentimes requiring use of an inserter instrument that can gape the wound or that may necessitate enlargement of the wound to accommodate the inserter instrument along with the implant.

Another available type of implant, an example of which is disclosed in U.S. Pat. No. 4,556,998—Siepser, is one made from a solid hydrophilic material that is hydrated by fluid in the eye, causing it to expand after implantation. Before such expansion, it is small enough to fit through the small incision. A problem with this type of implant is that there is a large degree of variability and unpredictability in the expansion dimensions of the implant, thus causing problems with centering and positioning the implant.

Still another approach to the basic problem of inserting the implant through a very small incision is to make the lens from a plurality of parts which are subsequently assembled together within the eye. Examples of this approach are disclosed in U.S. Pat. Nos. 4,636,210—Hoffer, 4,451,938—Kelman and 4,573,998—Mazzocco. This approach usually requires complicated and awkward means for holding together the parts of the final assembly and for positioning the final assembly or requires for assembling the parts awkward procedures involving the use of surgical tools within the eye, thus increasing the risk of accidental injury to the cornea, iris, or lens capsule.

OBJECTS

An object of my invention is to provide a simple intraocular lens implant that can be introduced and positioned through a very small incision in the eye.

Another object is to provide a lens implant of this type which consists of a plurality of components that are readily assembled within the eye and are held in assembled relationship by simple means that also fixes the Position of the lens within the eye.

Still another object is to provide a method of lens implantation that can be readily performed utilizing a very small incision.

Still another object is to provide a lens implantation method of the type set forth in the immediately-preceding paragraph, employing for the lens a plurality of components, and utilizing a simple, easy-to-deploy procedure for holding the components in assembled relationship and in a fixed position within the eye.

SUMMARY

In carrying out the invention in one form, T provide a method for implanting an artificial lens in an eye in which: (i) the crystalline portion of the natural lens has been surgically removed through a small incision in ocular tissue at the front of the eye, (ii) the anterior wall of the lens capsule has been provided with an opening therein, and (iii) the posterior wall of the lens capsule has been left intact. This method utilizes an expansible bag that has a transparent body portion containing a cavity and an entrance opening to said cavity through which filler material can be introduced into said body portion. The method is performed by inserting the body portion of the bag through said incision and through said opening in the anterior wall of the lens capsule into a position wherein at least a portion of the body portion is located within the still-remaining part of the lens capsule. Then the body portion is distended by introducing filler material through said entrance opening, and the distended body portion is located within the still-remaining portion of the lens capsule in a location adjacent the posterior wall of the capsule. Thereafter, the entrance opening to the cavity within the body portion may be closed off, and the incision in the ocular tissue is closed.

In one form of the invention, the filler material is a clear liquid with an appropriate index of refraction. In another form of the invention, the filler material includes a plurality of segments of transparent solid material that when assembled together form a lens-shaped member within the body portion of the bag.

The invention also relates to a lens implant as an article having the structure, use and characteristics set forth in the two immediately-preceding paragraphs.

BRIEF DESCRIPTION OF FIGURES

For a better understanding of the invention, reference may be made to the following detailed description taken in conjunction with the accompanying drawings wherein:

FIG. 3 is a lens implant embodying one form of the invention. This implant, which comprises an expandable bag, is shown in a distended condition and in a location outside the eye.

FIG. 4 shows the implant bag of FIG. 3 in a collapsed condition draped around a stylet in preparation for introduction into the eye.

FIG. 5 is an enlarged sectional view along the line 5—5 of FIG. 4.

DETAILED DESCRIPTION OF EMBODIMENTS AND METHOD

Figure 1:
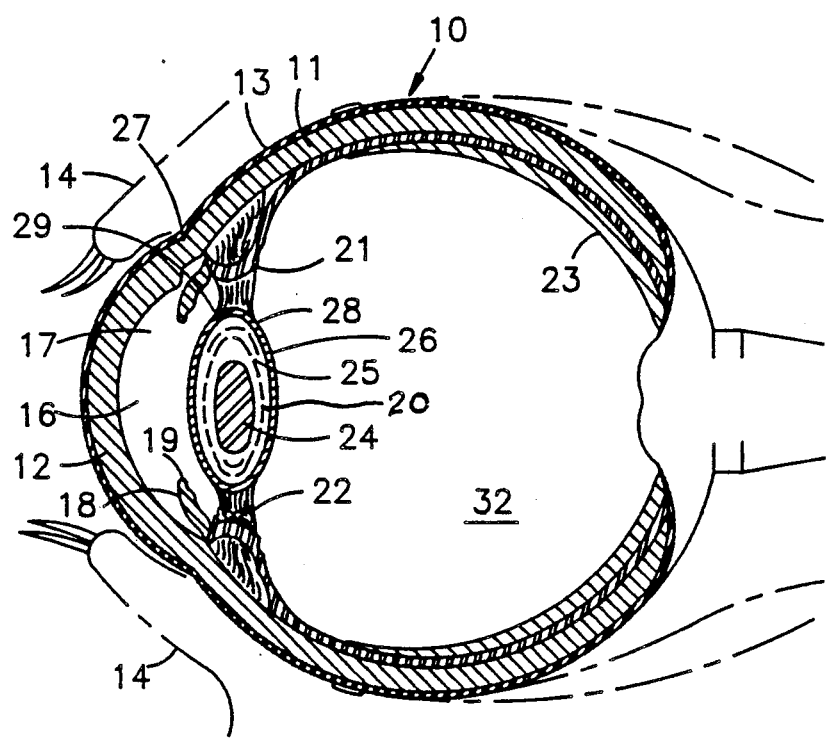
FIG. 1 is a side elevational view in half section of a human eye containing a natural lens.

Referring now to the drawings, and particularly to FIG. 1, the basic parts of the normal human eye 10 are illustrated. The outer coating or white of the eye, referred to as the sclera, is shown at 11. At the front of the eye there is a central portion 12 continuous with the sclera that is clear and is called the cornea.

Starting at the outer edge of the cornea 12 and covering the anterior portion of the sclera 11 is a thin, transparent membraneous layer 13 called the conjunctiva. The conjunctiva also folds backward to line the eyelids 14 so that the two surfaces glide over one another when the lids blink or the eye moves.

Directly behind the cornea is the anterior chamber 16. This chamber contains an aqueous fluid called the aqueous humor 17 which circulates nourishment and helps to maintain the correct pressure in the eye.

The iris 18, the colored portion of the eye, is located at the back of the anterior chamber 16. The iris 18 surrounds a central opening, or pupil 19. The muscles of the iris 18 dilate and contract the pupil 19 thereby regulating the amount of light entering the eye.

Behind the iris 18 is the crystalline lens 20 of the eye, which in a normal eye is clear, but cloudy if cataractous. A ring-like structure behind the outer edge of the iris 18, called the ciliary body 21, focuses the lens and manufactures the aqueous humor. Zonules 22 stretch from the ciliary body 21 to the lens 20 and hold the lens in place.

The back portion of the eye contains a large space between the lens 20 and the retina 23. This space contains vitreous humor 32, a jelly-like fluid which also helps to maintain the shape and the correct pressure within the eye.

The lens 20 comprises a hard inner nucleus 24 surrounded by jelly-like fibers called the cortex 25. The nucleus 24 and cortex 25 are encased in a thin elastic membrane 26 of elliptically-shaped cross-section referred to as the lens capsule. The lens capsule comprises a back wall 28, referred to herein as the posterior wall of the capsule, and a front wall 29, referred to as the anterior wall of the capsule.

A cataract condition is present when the material 24, 25 within the lens capsule 26 becomes cloudy. As the cloudiness of this material increases, its ability to transmit light is progressively reduced, and vision becomes progressively blurrier.

Figure 2:
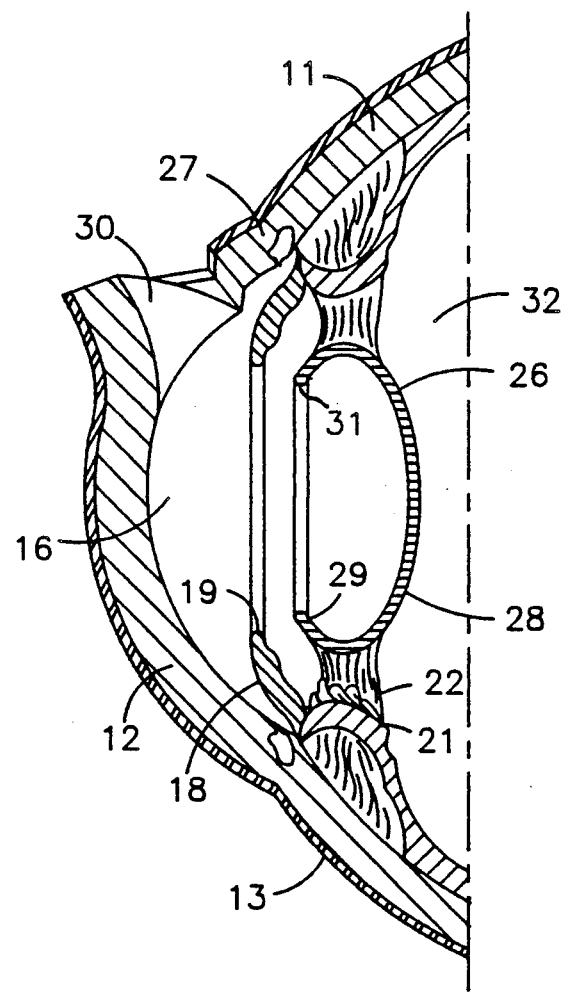
FIG. 2 is an enlarged side elevational view in half section of the front portion of the eye of FIG. 1 after surgery has been performed to remove the crystalline portion of the natural lens.

This condition can be remedied by surgically removing the cloudy material 24, 25, which is referred to as a cataract, and replacing it with an artificial lens. In extracapsular cataract extraction, the surgeon first makes an incision 30 (see FIG. 2) in the limbus region 27 at the edge of the cornea and inserts through this incision 30 and the then-dilated pupil 19 a suitable surgical instrument that he uses for making a relatively large, generally circular opening 31 in the front wall 29 of the lens capsule. He can then use for removing the opacified lens nucleus 24, a hollow phaco-emulsification probe or needle, which he inserts through the incision 30 and the dilated pupil 19 into contact with the nucleus 24. Through this probe ultrasonic vibrations are applied to the opacified, hard nucleus 24, fragmenting it into small particles. These particles are then removed by suction through the hollow phaco-emulsification probe. Then the phaco-emulsification probe is removed by withdrawing it through the incision 30; and a hollow aspiration and irrigation tip is inserted through the incision into the lens region. The cortex portion 25 is then dislodged from the lens capsule 26 by liquid supplied through the tip, following which this cortex material is aspirated through the hollow tip, leaving the interior of the lens capsule 26 clean. Then the hollow tip is withdrawn through the incision 30. After these steps have been performed, the front part of the eye has the cross-sectional appearance shown in FIG. 2, where it can be seen that posterior wall 28 of the lens capsule 28 is essentially intact and the anterior wall 29 of the lens capsule has the large opening 31 therein. The portion of the anterior wall 29 that remains forms an annular flap surrounding this opening. All of the surgical instruments used for removing the cataract as described in this paragraph can readily be employed using a small incision 30 of only 3 or 4 mm in length.

The intraocular lens implant, designated 40, is shown in cross-section in FIG. 3. For illustrative purposes, it is shown in FIG. 3 located outside the eye and filled with a clear viscous liquid 41. The implant may be thought of as a bag comprising a hollow body portion 42 and a hollow neck portion 44 containing a passage communicating with the interior cavity of the body portion via an entrance opening 46. The bag is of a thin, soft, flexible, transparent, inert, biocompatible material with appropriate tensile strength to enable it to serve as a reliable container for a filler material. Examples, among others, of such bag material are thin transparent materials of one of the following: polyethylene terephthalate, polypropylene, and polyvinyl chloride. The body portion 42 comprises a flexible posterior face 50, a flexible anterior face 52, and an outer peripheral region 54 joining these two faces. The outer peripheral region 54 is of the same material as the flexible faces but is thicker and firmer than the faces, and this enables the outer peripheral region to act as a positioning and stabilizing ring for holding the body portion in a stable position when positioned within the lens capsule 26, as will soon be described in more detail.

For limiting separation of the faces 50 and 52 and for maintaining their desired shape, a plurality of fine strands 58 of a suitable plastic material, perferably the same material as used for the bag, are connected between these two faces. In one embodiment, these strands are present in two rows, the strands in each row being substantially vertically aligned.

Figure 6:
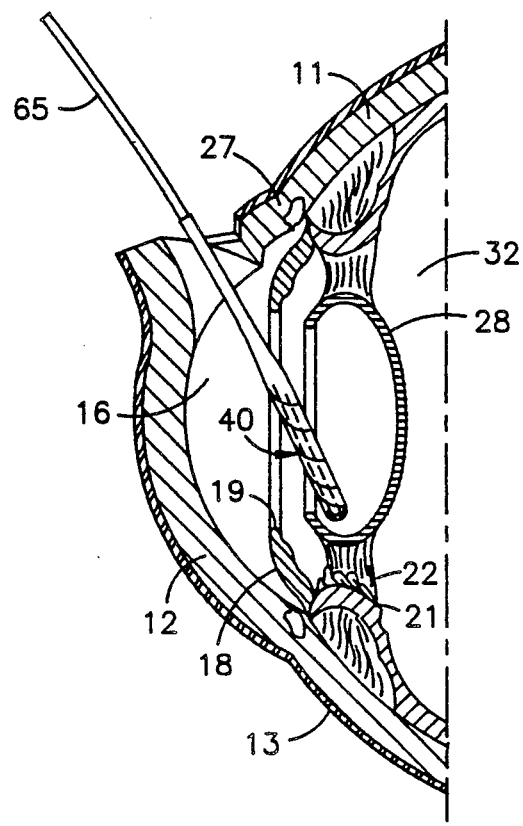
FIG. 6 shows the stylet and implant bag of FIG. 4 after the forward tip of stylet has been inserted into the bottom of the lens capsule but before distension of the bag.

Before the bag 40 is introduced into the eye, it is in an uninflated, or collapsed, state. To prepare for the insertion operation, a thin blunt-tipped hollow rod, or stylet, 65 is inserted into the bag through its neck portion, and the bag is draped about the stylet as shown in FIG. 4. In one embodiment of the invention, the stylet 65 is hollow so as to provide a passage 67 along its length through which liquid can be introduced via entrance opening 46 into the cavity in body portion 42 of the hag. Passage 67 is open at its opposite ends to provide an outlet at its forward end and an inlet at its back end. The combination of the stylet 56 and collapsed bag draped about it has the cross-sectional form shown enlarged in FIG. 5. The external diameter of this combination is sufficiently small that it can easily be inserted through the small incision 30, which is only 3 or 4 mm in length, without enlarging the incision. The forward end of the stylet 65 is carefully guided through the pupil 19 into a position at the bottom of the lens capsule 26, locating the forward end of bag 40 in this position, as shown in FIG. 6.

Figure 7:
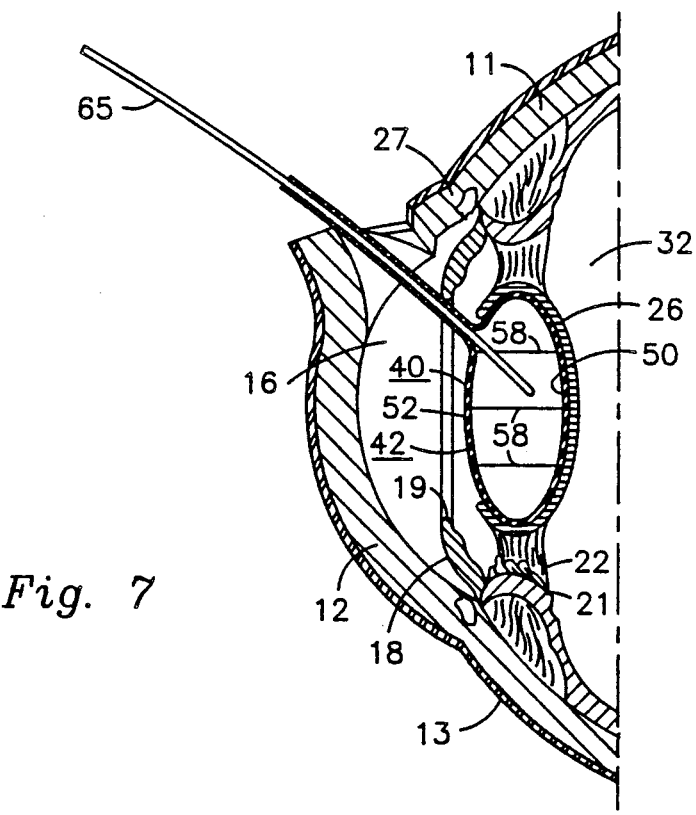
FIG. 7 shows the same parts as illustrated in FIG. 6 but after distension of the bag in accordance with one form of the invention.

Next, liquid is introduced into the cavity within body portion 42 of bag 40 through the passage 67 in the stylet 65, entering through the back end of the passage 67 and exiting through its forward end, and causing the body portion 42 of the bag to expand into its form shown in FIG. 7. The stylet 65 is lifted and tilted during such expansion to assist the bag 40 in assuming the position shown in FIG. 7. When the bag has been distended to its condition of FIG. 7, body portion 42 fills the still-remaining portion of the lens capsule 26 and is thus firmly anchored in place within the lens capsule. The strands 58 act to maintain the form of the body portion 42 of the bag when the bag is filled.

A liquid that may be used for filling the bag is the high molecular-weight, clear, visco-elastic, sterile liquid sold by Pharmacia, Pasadena, Calif. under its trademark HEALON. Such liquid is a solution of sodium hyaluronate, sodium chloride, disodium hydrogen phosphate dihydrate, sodium dihydrogen phosphate hydrate, and water. Other liquids which may be used for this purpose include, by way of example and not limitation, the visco-elastic liquid sold by Cooper Vision/Cilco, Belleview, Wash. under its trademark VISCOATE or a liquid with similar properties sold by Iolab, Claremont, Calif. under its trademark AMVISC. The liquid carrying the VISCOAT trademark is a solution of the following: sodium chondroitin sulfate, sodium hyaluronate, sodium dihydrogen phosphate hydrate, disodium hydrogen phosphate, sodium chloride, and water. The liquid carrying the AMVISC trademark is a solution of sodium hyaluronate, sodium chloride, and water. The index of refraction of the liquid filler material can be adjusted by including therein an appropriate additive that is transparent, biocompatible, and has a suitable optical density. By adjusting the percentage of the additive that is included, this index of refraction is adjusted to meet the needs of the particular eye that is being operated upon.

After the bag has been distended as shown in FIG. 7, its neck portion 44 is closed off immediately adjacent the body portion 42 of the bag either by a suitable suture or surgical knot or by a suitable thermal sealing process. The region of the neck portion beyond the resulting seal and extending through the incision 30 is detached and removed through the incision 30. When the iris 18 is allowed to return to its normal position, it covers the site of the seal, and the seal is sufficiently remote from the central region of the lens that it does not substantially interfere with the normal passage of light therethrough.

Although FIGS. 3-7 show the bag 40 as having a neck portion 44 that is long enough to extend through the incision 30, it is to be understood that a much shorter neck portion can be used. The longer neck portion facilitates the above-described handling of the implant and tie-off of the neck portion, but these steps can still be performed using a shorter length neck portion and in some cases even without a neck portion.

The above-described filling of the bag 40 and the closing off of the neck portion 44 are performed through the incision 30 and can readily be so performed without enlarging this 3 or 4 mm incision, thus enabling the entire cataract replacement operation to be performed through this small incision, in accordance with the objectives of this invention. After the body portion 42 of the bag 40 is filled and closed off as above-described, the operation is completed in a conventional manner, employing procedures that involve closing the incision 30 with a suture or other conventional means.

Another way of controlling the converging power of the implanted lens is by controlling the amount of liquid introduced into the body portion 42 of the bag. Generally speaking, the greater the amount of such liquid introduced, the more spherical the lens becomes and, hence, the greater its converging power. It is to be understood that ii this approach is used, the strands 58 must be designed with sufficient yield to allow for these adjustments in the sphericity of the lens. It is to be further understood that the converging power of the lens can be adjusted by relying upon this approach alone or in combination with the above-described approach of adjusting the index of refraction of the injected liquid.

Figure 8:
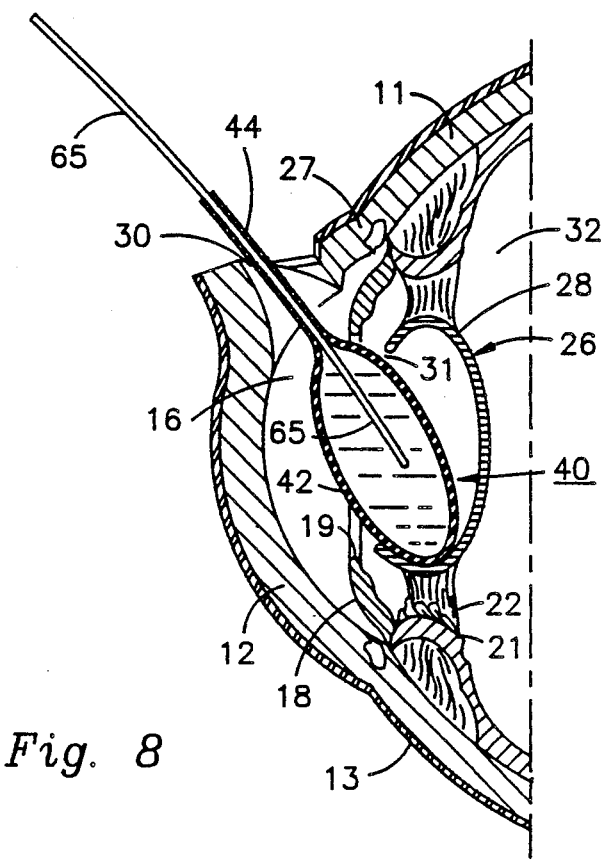
FIG. 8 shows the same parts as illustrated in FIG. 6 but after distension of the bag in accordance with another form of the invention

In the above-described embodiment, I carry out the bag distending procedure while the body portion 42 of the bag is located entirely within the lens capsule 26. In another embodiment, I orient the bag 40 after it is positioned as in FIG. 6, so that during distension its upper portion projects through the opening 31 in the anterior wall 29 of the lens capsule 26 and the pupil 19, as shown in FIG. 8. Then after distension is completed and the neck portion sealed off, as above-described, the upper portion of the bag is pressed into place within the lens capsule. An advantage of this approach of FIG. 8 is that the junction between the neck portion 44 and the body portion 42 of the bag can be located at the outer periphery of the body portion. As a result, when the neck portion is sealed off, the resulting seal is located at the outer periphery of the body portion and is thus in a position where it is less likely to disturb passage of light through the crucial central region of the lens.

Figures 9, 10:
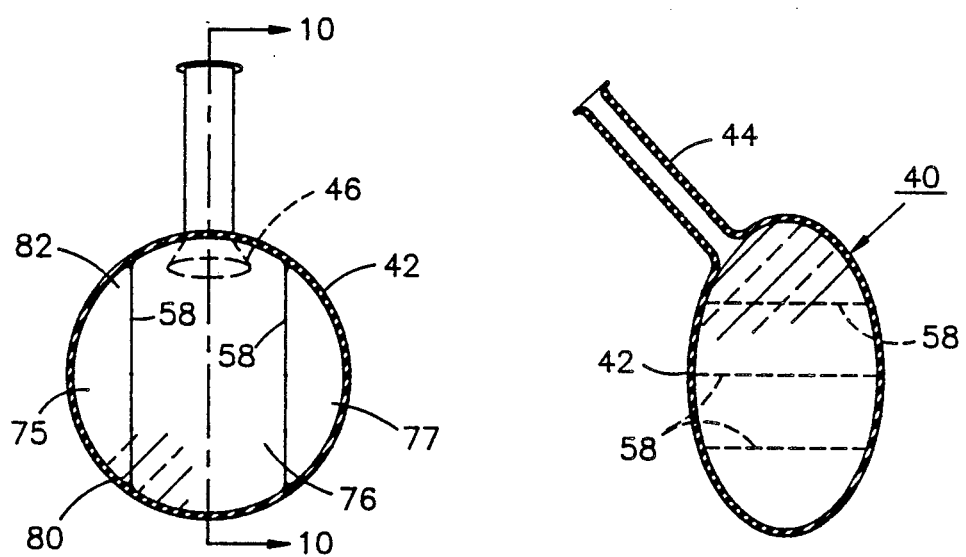
FIG. 9 is an enlarged sectional view of a modified lens implant. This modified implant comprises an expandable bag and a plurality of plastic segments therein.
FIG. 10 is a sectional view taken along the line 10—10 of FIG. 9.

In another embodiment of the invention, illustrated in FIGS. 9 and 10, I use as a filler for the bag 40 a plurality of solid segments which when assembled together form a lens-shaped member within the bag. In this embodiment, the bag 40 is draped about a stylet 65 and inserted through incision 30 into the position of FIG. 6, just as in the previously described embodiments. Then the bag is distended, as shown in FIG. 7, with a sterile visco-elastic or physiological balanced saline solution, e.g. of a type that is now commonly used during intraocular surgery, or other suitable liquid. Then, a plurality of plastic segments are introduced via neck portion 44 and entrance opening 46 into the cavity within body portion 42 of the bag. Referring to FIGS. 9 and 10, these segments are illustrated at 75, 76 and 77. Upon introduction, each segment displaces a portion of the solution then present within the bag, expelling this displaced solution through the neck portion 44.

Using appropriate forceps, one of the end segments 75 is first introduced lengthwise through the entrance opening 46 with its lower end 80 preceding its upper end 82. Upon entering the cavity within body portion 42, this segment 75 is guided over the upper strands 58 and into its seated position of FIGS. 9 and 10. Then the other end segment 77 is introduced in substantially the same manner and is guided into its seated position of FIGS. 9 and 10. Thereafter, the centrally located segment 76 is introduced through the neck portion 44 and entrance opening 46 and is guided into place between the already-present end segments 75 and 77.

When all three segments 75, 76 and 77 have thus been introduced, they collectively form a biconvex lens-shaped member that fills the body portion of bag 40. As shown in FIGS. 9 and 10, the juxtaposed faces of the segments are planar and parallel so that they fit closely together. While strands 58 are positioned between these faces, these strands are fine strands disposed parallel to the faces, thus reducing to a near minimum the spacing between the faces, thereby reducing any boundary problems such as glare. Moreover, because the lens-shaped member is divided into three segments with a relatively wide central segment, there are no boundaries or other discontinuities in the central region of the lens. This central region of the lens is, of course, the most important region of the lens from a light-transmission and vision standpoint.

The width of each of the segments 75, 76 and 77 is made substantially less than 3 or 4 mm so that each segment will fit through the 3 or 4 mm incision 30 without enlarging it. (For example, the central segment is about 2.5 mm in width and each of the end segments is slightly less than 2 mm in maximum width.) This enables a composite lens-shaped member 75, 76, 77 that is 6 mm in diameter or slightly greater to be assembled within the body portion 42 of bag 40 despite the substantially smaller 3 or 4 mm size of the incision 30.

In one form of the invention, the lens segments 75, 76 and 77 are of polymethylmethacrylate, a clear, hard plastic material that is commonly used for lens implants. Other usable solid materials are suitable silicones or hydrogels.

Although I have shown in FIGS. 9 and 10 a bag 40 including a hollow neck (44), my invention in its broader aspects can be practiced using a bag having no such neck but rather a slit opening near the outer periphery of body portion 42 through which solid segments such as 75, 76 an 77 can be introduced into the cavity within body portion 42.

In the above-described embodiments, the bag 40 remains in place within the lens capsule 26 when the operation has been completed. In a modified form of the invention, I use the bag 40 primarily to facilitate location and assembly of the solid segments 75, 76, 77 within the lens capsule but withdraw the bag through the incision 30 before the operation is completed. In this modified form, the solid segments are fused or otherwise joined together before the bag 40 is withdrawn, thus creating a monolithic solid lens that is capable of remaining precisely located within the lens capsule 26 despite withdrawal of the bag. The fusing or joining of the segments is carried out while they are still surrounded by the bag.

While 1 have shown and described particular embodiments of my invention, it will be obvious to those skilled in the art that various changes and modifications may be made without departing from my invention in the broader aspects; and 1, therefore, intend in the appended claims to cover all such changes and modifications as fall within the true spirit and scope of my invention.

What I claim is:

1. A method for implanting an artificial lens in an eye in which the crystalline portion of the natural lens has been surgically removed through a small incision in ocular tissue at the front of the eye, the anterior wall of the lens capsule has an opening therein, and the posterior wall of the lens capsule is intact, the method comprising the steps of:
   (a) providing an expansible bag that has a transparent body portion containing a cavity and an entrance opening to said cavity portion through which filler material can be introduced into said body portion,
   (b) inserting the body portion of said bag through said incision and said opening in the anterior wall of the lens capsule into a position wherein at least a portion of the bag is located within the still-remaining part of the lens capsule,
   (c) distending said body portion with liquid filler material introduced through said entrance opening and locating said distending body portion in the still-remaining part of the lens capsule in a location adjacent said posterior wall,
   (d) after said inserted body portion has been distended by said introduced liquid filler material, sealing said entrance opening by thermally sealing the bag material immediately adjacent said entrance opening, and
   (e) closing said incision.

2. The method of claim 1 in which said distending of said body portion of the bag is effected by introducing a transparent liquid into said body portion through said entrance opening.

3. The method of claim 2 in which the converging power of the implanted lens is adjusted by adding to the liquid in said body portion a second liquid having a different index of refraction from said first liquid.

4. The method of claim 2 in which the observing power of the implanted lens is adjusted by controlling the amount of liquid introduced into said body portion thereby to control the curvature of the lens surfaces.

5. A method for implanting an artificial lens in an eye in which the crystalline portion of the natural lens has been surgically removed through a small incision in ocular tissue at the front of the eye, the anterior wall of the lens capsule has an opening therein, and the posterior wall of the lens capsule is intact, the method comprising the steps of:
  (a) providing an expansible bag that has a transparent body portion containing a cavity and an entrance opening to said cavity portion through which filler material can be introduced into said body portion,
  (b) inserting the body portion of said bag through said incision and said opening in the anterior wall of the lens capsule into a position wherein at least a portion of the bag is located within the still-remaining part of the lens capsule,
  (c) distending said body portion with filler material introduced through said entrance opening and locating said distended body portion in the still-remaining part of the lens capsule in a location adjacent said posterior wall, and
  (d) closing said incision, and in which:
  (e) said filler material includes segments of solid transparent material that are introduced through said entrance opening and that fit together when located in said body portion and collectively form a lens-shaped member.

6. The method of claim 5 in which:
  (a) said body portion includes a flexible posterior face, a flexible anterior face, an outer peripheral region joining said anterior and posterior faces, and strands extending between said anterior and posterior faces,
  (b) said segments have juxtaposed surfaces when the segments are assembled into said lens-shaped member, and
  (c) said segments are assembled in such a manner that said juxtaposed surfaces extend parallel to said strands.

7. The method of claim 5 in which said segments after being located within said body portion are joined together and said bag is withdrawn from the eye.

8. A method for implanting an artificial lens in an eye in which the crystalline portion of the natural lens has been surgically removed through a small incision in ocular tissue at the front of the eye, the anterior wall of the lens capsule has an opening therein, and the posterior wall of the lens capsule is intact, the method comprising the steps of:
  (a) providing an expansible bag that has a transparent body portion containing a cavity and an entrance opening to said cavity portion through which filler material can be introduced into said body portion,
  (b) inserting the body portion of said bag through said incision and said opening in the anterior wall of the lens capsule into a position wherein at least a portion of the bag is located within the still-remaining part of the lens capsule,
  (c) distending said body portion will filler material introduced through said entrance opening and locating said distended body portion in the still-remaining part of the lens capsule in a location adjacent said posterior wall, and
  (d) closing said incision, and in which:
  (e) said body portion includes a flexible posterior face, a flexible anterior face, an outer peripheral region joining said anterior and posterior faces, and strands extending between said anterior and posterior faces, and
  (f) said strands are utilized for limiting the spacing between said faces of the body portion when the body portion is distended.

9. The method of claim 8 in which said distending of said body portion of the bag is effected by introducing a transparent liquid into said body portion through said entrance opening.

10. The method of claim 9 in which after said body portion has been distended by said introduced liquid filler material, said entrance opening is sealed.

11. A method for implanting an artificial lens in an eye in which the crystalline portion of the natural lens has been surgically removed through a small incision in ocular tissue at the front of the eye, the anterior wall of the lens capsule has an opening therein, and the posterior wall of the lens capsule is intact, the method comprising the steps of:
  (a) providing an expansible bag that has a transparent body portion containing a cavity and an entrance opening to said cavity portion through which filler material can be introduced into said body portion,
  (b) inserting the body portion of said bag through said incision and said opening in the anterior wall of the lens capsule into a position wherein at least a portion of the bag is located within the still-remaining part of the lens capsule,
  (c) distending said body portion with filler material introduced through said entrance opening and locating said distended body portion in the still-remaining part of the lens capsule in a location adjacent said posterior wall, and
  (d) closing said incision, and in which:
  (e) prior to insertion of said body portion into said lens capsule, a thin rod having a blunt tip to inserted into said bag, the bag is draped about said rod,
  (f) the insertion of step (b) is performed by inserting said rod with the bag draped thereabout through said incision and through said opening in the anterior wall of the lens capsule, and
  (g) said rod is thereafter removed and said distended body portion is allowed to remain within the still remaining part of the lens capsule.

12. The method of claim 11 in which:
  (a) said rod has a passage extending along its length, and
  (b) said body portion is distended by introducing liquid through said passage into said cavity within said body portion.

13. The method of claim 11 in which:
  (a) said bag has a neck portion joined to said body portion at said entrance opening, and
  (b) said body portion is distended by introducing liquid through said neck portion.

14. The method of claim 13 in which said neck portion is provided with a seal after said distension that closes off said body portion.

15. The method of claim 14 in which most of said neck portion is removed after said seal has been provided.

16. Apparatus for providing an artificial lens in an eye in which: (i) the crystalline portion of the natural lens has been surgically removed through a small incision in ocular tissue at the front of the eye, (ii) the lens capsule has been prepared for said artificial lens by providing an opening in the anterior wall of the lens capsule, and (iii) the posterior wall of the lens capsule has been left intact, the apparatus comprising:

(a) a collapsible and expansible bag that comprises a transparent body portion containing a cavity and an entrance opening to said cavity through which filler material can introduced into said body portion, said body portion being adapted to fit within the surgically-prepared lens capable of said eye in a position adjacent the posterior wall of the lens capsule when expanded by filler material introduced thereinto via said small incision and said entrance opening, and (b) a thin rod having a passage extending along its length and also having a blunt tip that is inserted into said bag prior to insertion of said body portion into said lens capsule, the bag then being draped about said inserted rod, the apparatus being further characterized by:

(c) the body portion of said bag and the tip of said rod being insertable together through said incision and the opening in the anterior wall of the lens capsule while said bag is draped about said rod, thereby to position the body portion of said bag and said rod tip in said surgically-prepared lens capsule, and, (d) said body portion being expandable to substantially fill and lens capable in response to the introduction of liquid filler material into said body portion through said passage in said rod.

17. Apparatus as defined in claim 16 and further comprising filler material for said body portion introducable into said body portion through said entrance opening.

18. The apparatus of claim 17, in which said filler material is a transparent liquid.

19. The apparatus lens implant of claim 18 in which said transparent liquid contains a plurality of liquid components having different indices of refraction, the proportions of which can be controlled to control the converging power of the lens.

20. The apparatus of claim 18 in which the curvature of a lens surface is adjusted by controlling the amount of liquid filler material that is introduced into said body portion, thereby controlling the converging power of the lens.

21. The apparatus of claim 16 in, which said body portion includes a flexible posterior face for juxtaposition with the posterior wall of said lens capsule, a flexible anterior face, and an outer peripheral region joining said anterior and posterior faces, the outer peripheral region being firmer than said faces to render said region capable of acting as a positioning ring for holding said body portion in a stable position within said lens capsule when expanded by said filler material.

22. An intraocular lens implant for insertion into the surgically-prepared lens capsule of a human eye after the crystalline portion of the natural lens has been removed from said capsule through a small incision to ocular tissue at the front of the eye, said lens implant comprising:

(a) a collapsible and expansible bag that comprises a transparent body portion containing a cavity and an entrance opening to said cavity through which filler material can be introduced into said body portion, (b) said body portion being adapted to fit within the surgically-prepared lens capsule of said eye in a position adjacent the posterior wall of the lens capsule when expanded by filler material introduced therein via said small incision and said entrance opening, and (c) filler material for said body portion introducible into said body portion through said entrance opening, said filler material comprising segments of solid transparent material that fit together when located in said body portion and collectively form a lens-shaped member, each of which segments being of such size that it can be fitted through said entrance opening and also through said small incision without lengthening the incision.

23. The lens implant of claim 22 in which:
(a) said body portion includes a flexible posterior face for juxtaposition with the posterior wall of said lens capsule, a flexible anterior face, and strands extending between said posterior and anterior faces,
(b) said segments have juxtaposed surfaces when the segments are assembled into said lens-shaped member, and
(c) said segments are assembled in such a manner that said juxtaposed surfaces extend parallel to said strands.

24. The lens implant of claim 22 in which:
(a) said body portion includes a flexible posterior face for juxtaposition with the posterior wall of said lens capsule, a flexible anterior face, and strands extending between said posterior and anterior faces,
(b) said segments have juxtaposed surfaces when the segments are assembled into said lens-shaped member,
(c) said segments are assembled in such a manner that said juxtaposed surfaces extend parallel to said strands, and
(d) one of said segments is a centrally-located segment that defines an uninterrupted central region for the lens-shaped member.

25. The lens implant of claim 24 in which said centrally-located segment is wider than the other segments of said lens-shaped member.

26. An intraocular lens implant for insertion into the surgically-prepare lens capsule of a human eye after the crystalline portion of the natural lens has been removed from said capsule through a small incision in ocular tissue at the front of the eye, said lens implant comprising:

(a) a collapsible and expansible bag that comprises a transparent body portion containing a cavity and an entrance opening to said cavity through which filler material can be introduced into said body portion, and (b) said body portion being adapted to fit within the surgically-prepared lens capsule of said eye in a position adjacent the posterior wall of the lens capsule when expanded by filler material introduced thereinto via said small incision and said entrance opening, and in which said body portion further includes: (i) a flexible posterior face for juxtaposition with the posterior wall of said lens capsule, (ii) a flexible anterior face, and (iii) strands extending between said posterior and anterior faces for limiting the spacing between said faces when the body portion is expanded by filler material introduced therein.

27. The lens implant of claim 26 in which said body portion further includes an outer peripheral region joining said anterior and posterior faces, the outer peripheral region being firmer than said faces to render said region capable of acting as a positioning ring for holding said body portion in a stable position within said lens capsule when expanded by said filler material.

* * * * *